United States Patent [19]

Cormier et al.

[11] 4,369,127
[45] * Jan. 18, 1983

[54] BLOOD GAS CONTROL

[75] Inventors: Alan D. Cormier, Newburyport; Marvin Feil, Brookline; Kenneth D. Legg, Wellesley, all of Mass.

[73] Assignee: Instrumentation Laboratory Inc., Lexington, Mass.

[*] Notice: The portion of the term of this patent subsequent to Nov. 10, 1998, has been disclaimed.

[21] Appl. No.: 241,600

[22] Filed: Mar. 9, 1981

Related U.S. Application Data

[63] Continuation-in-part of Ser. No. 170,600, Jul. 21, 1980, Pat. No. 4,299,728.

[51] Int. Cl.³ .................. G01N 33/48; C09K 3/00; B01J 13/00; G01N 33/00
[52] U.S. Cl. .................. 436/111; 252/312; 252/408.1; 422/36; 424/2; 424/3
[58] Field of Search .......... 252/408, 312; 23/230 B, 23/232 R; 424/2, 3, 352, 339, 342, 350, 325; 422/36

[56] References Cited

U.S. PATENT DOCUMENTS

| | | | |
|---|---|---|---|
| 3,629,142 | 12/1971 | Marback | 252/408 |
| 3,681,255 | 8/1972 | Wilfore | 252/408 |
| 3,778,381 | 12/1973 | Rosano et al. | 252/408 |
| 3,823,091 | 7/1974 | Samejima et al. | 252/408 |
| 3,911,138 | 10/1975 | Clark, Jr. | 252/408 |
| 3,973,413 | 8/1976 | Louderback | 252/408 |
| 3,993,581 | 11/1976 | Yokoyama et al. | 252/408 |
| 4,001,142 | 1/1977 | Turner | 252/408 |
| 4,116,336 | 9/1978 | Sorensen et al. | 252/408 |
| 4,151,108 | 4/1979 | Sorensen et al. | 252/408 |
| 4,163,734 | 8/1979 | Sorensen et al. | 252/408 |
| 4,199,471 | 4/1980 | Louderback et al. | 252/408 |
| 4,289,648 | 9/1981 | Hoskins et al. | 252/408 |
| 4,299,728 | 11/1981 | Cormier et al. | 252/408 |

FOREIGN PATENT DOCUMENTS

| | | | |
|---|---|---|---|
| 1343870 | 1/1974 | United Kingdom | 252/408 |
| 1445925 | 8/1976 | United Kingdom | 252/408 |
| 1459824 | 12/1976 | United Kingdom | 252/408 |
| 1517024 | 7/1978 | United Kingdom | 252/408 |
| 1555626 | 11/1979 | United Kingdom | 252/408 |

OTHER PUBLICATIONS

Mass, A. H. J., et al., Clin. Chem., vol. 23, No. 9, pp. 1718-1725 (1977).
Clark, Jr., et al., Ala. J. Med. Sci., vol. 9, No. 1, pp. 16-29 (1972).
"The Merck Index", 8th Ed., Merck & Co., Inc., Rahway, N. J., p. 469 (1968).

*Primary Examiner*—Teddy S. Gron

[57] ABSTRACT

A blood gas control liquid comprises a stable oil-in-water emulsion that has an oxygen solubility coefficient of at least 10 ml $O_2$ per 100 ml emulsion and a viscosity of less than 10 centipoises. The emulsion includes water, 5-40 percent by volume of a water-insoluble non-protein compound material, 0.25-10 percent by volume of a nonionic surfactant, a pH buffering agent and a preservative agent which is substantially non-reactive with the pH buffering agent. A preferred blood gas control liquid has a density of about 1.08. The blood gas control liquid has a pH in the range of 7-8, a partial pressure of carbon dioxide in the range of 15-80 millimeters Hg, and a partial pressure of oxygen in the range of 20-600 mm Hg.

21 Claims, No Drawings

BLOOD GAS CONTROL

This application is a continuation-in-part of our copending patent application Ser. No. 170,600 filed July 21, 1980, now U.S. Pat. No. 4,299,728.

This invention relates to blood gas control liquids for quality control and/or calibration of blood gas analyzer equipment.

Blood gas analyzers are utilized to measure parameters of blood such as pH, partial pressure of carbon dioxide (expressed as $pCO_2$), and partial pressure of oxygen (expressed as $pO_2$). Such blood gas analyzers require frequent calibration and quality control checks to insure the analyzer is operating properly and accurately. In connection with such quality control and calibration procedures, it is convenient to use a prepared blood gas control liquid of constant, known composition to monitor the accuracy of such analyzers. For practical purposes, the blood gas control liquid should have long term physical and chemical stability, constant pH, $pCO_2$, and $pO_2$ levels, flow characteristics comparable to blood, and should be readily cleaned from and not otherwise complicate or impair analyzer accuracy. Commercially available, prepared aqueous blood gas control liquids adequately mimic blood for pH and $pCO_2$, but do not have adequate oxygen buffering capacity as they are unable to dissolve an adequate amount of oxygen. Such controls are therefore prone to inaccuracy in the presence of relatively small amounts of outside oxygen contamination, and also may falsely indicate certain types of instrument malfunctions.

Other blood gas control products have been proposed which are based on components of human blood (e.g., Louderback U.S. Pat. No. 3,973,913) or components proposed for use as blood substitutes such as fluorocarbon and silicone compound emulsions (e.g., Sorenson et al. U.S. Pat. No. 4,163,734). One blood gas control product proposed by Sorenson et al. contains a perfluorotributylamine compound, an emulsifying agent to provide a stable suspension of the perfluorinated compound, a phosphate buffer system, and a bicarbonate ion-carbon dioxide buffer system. Sterilization, which is necessary for stability, is accomplished by means of radioactive irradiation. Such a control liquid has several undesirable limitations. A perfluorotributylamine-water emulsion with an oxygen solubility coefficient of ten requires a high fluorocarbon:water ratio (in excess of 20% fluorocarbon) which results in an undesirable viscosity that is much higher than that of blood. The emulsion leaves bubbles in the measuring chambers of blood gas analyzer equipment, creating cleaning difficulties and causing control-to-sample carry over. The specific surfactant described in Sorenson et al., like all polyol surfactants, must be used in an amount that further undesirably increases viscosity. Also the phosphate buffer system is conducive to growth of aerobic bacteria, which impair $pO_2$ stability, and efforts to sterilize the product by means of radioactive irradiation are themselves detrimental to oxygen stability.

We have discovered a superior blood gas control liquid that includes a stable oil in water emulsion that has an oxygen solubility coefficient of at least 10 ml $O_2$ per 100 ml emulsion and a viscosity in the range of blood (a viscosity of less than 10 centipoises). The emulsion includes water, a water insoluble non-protein organic compound, and a nonionic surfactant that is partially soluble in both the water and the oil phases. The control liquid also includes a pH buffering agent and a microbial growth inhibiting agent that is substantially nonreactive with the buffering agent. Control liquids in accordance with the invention have emulsions of long term stability (at least six months without breaking), superior oxygen buffering capacity, good pH buffering and viscosity of less then ten centipoises.

Preferred control liquids are formulated to provide pH, $pCO_2$, and $pO_2$ values at three different levels (acidosis, normal, and alkalosis) and include coloring agents that simulate, both visually and analytically, corresponding hemoglobin value ranges, the acidosis level liquid having the appearance of normal venous blood, the normal level liquid having the appearance of normal arterial blood, and the alkalosis level liquid have the appearance of a low hemoglobin, high $pO_2$ blood, and each of these control liquids providing distinctive hemoglobin values when measured with hemoglobin analyzers. The density (at 20° C.) of a preferred blood gas control liquid is less than 1.12. Microbial growth in the liquids is discouraged without the use of irradiation or expensive sterile fill procedures; the liquids do not foam or form bubbles to a significant degree; and they are easily cleaned out of blood gas measuring equipment.

Blood gas control liquids in accordance with the invention are preferrably supplied enclosed in gas-tight, sealed ampuls and contain known concentrations of dissolved carbon dioxide and oxygen. A preferred liquid includes a water-based emulsion containing a water-insoluble perfluorinated compound material, a fluorocarbon-based surfactant capable of emulsifying the perfluorinated compound material, a preservative in a concentration sufficient to inhibit microbial growth without interfering with the quality control functions of the liquid, and a pH buffering agent substantially non-reactive with said preservative.

According to the invention, the perfluorinated compound material must have a high enough oxygen solubility coefficient, and be present in sufficient quantity, to yield a blood gas control liquid having an effective oxygen solubility coefficient of at least 10 ml $O_2$/100 ml of emulsion. Further, the perfluorinated compound material must have a high enough oxygen solubility coefficient to allow it to be used in an amount which constitutes less than about 40% of the liquid by volume, because larger volumetric amounts would raise viscosity to an unacceptable level. To provide a margin of safety, the effective oxygen coefficient of the perfluorinated compound material used in the invention should be, at one atmosphere pressure, 25° C., and a volumetric proportion of 15%, at least 10 mL $O_2$/100 mL emulsion.

A preferred perfluorinated compound material of the invention is manufactured by 3M Company under the designation "FC-77" and is a mixture of perfluoroalkanes and perfluorocyclic ethers. We have found that FC-77 may be advantageously used in combination with perfluorotributylamine, sold by 3M Company under the designation "FC-43" and/or with a dimethyl siloxane polymer that has a density of about 0.8 grams per milliliter, sold by Dow-Corning under the designation "200 Fluid-1 centistoke" (hereinafter "200-1"). Oil in water emulsions of these materials have the oxygen solubility coefficients shown in Table I below. Preferred fluorocarbon-based surfactants of the invention include fluoroalkylpoly(ethyleneoxy)ethanol, sold by DuPont Corporation under the designation Zonyl FSN; fluoracylpolyoxyethylene, sold under the designation Lodyne S-107 by Ciba-Geigy; fluorinated acylpolyoxyethylene ethanol, sold under the designation FC-170-C by 3M Company; and Monflor 51, a polymer of about 20–25 units of polyethyleneoxide with between one and four tetrafluoroethylene groups at each end, sold by Imperial Chemical Industries Ltd.

TABLE I

VOLUME SOLUBILITY IN ml $O_2$ ml EMULSION
(at one atmosphere and 25° C.)

| | % Oil in Water | | |
|---|---|---|---|
| | 10% | 15% | 20% |
| 200-1 | 4.12% | 4.78 | 5.44 |
| FC 43 | 6.12 | 7.78 | 9.44 |
| FC 77 | 8.12 | 10.78 | 13.44 |
| 3 FC 77 -1 FC 43 | 7.62 | 10.03 | 12.44 |

The buffering agent used in the invention is selected so that it is substantially non-reactive with the preservative being used. Because the preferred preservatives are the aldehydes, and particularly formaldehyde and gluteraldehyde, the preferred buffering agents are those containing a tertiary amine; such buffering agents do not react with aldehydes, and also are relatively non-conducive to microbial growth. The preferred tertiary amine buffering agent for use with an aldehydic preservative is HEPES (N-2-Hydroxyethyl-piperazine-N′-2-ethane sulfonic acid), its pK being centered in the appropriate physiological pH range. Another effective tertiary amine buffering agent for use with aldehydic preservatives is triethanolamine.

The blood gas control liquids are preferrably formulated to simulate three physiological levels of pH, $pCO_2$, and $pO_2$ values; and have coloring agents that simulate hemoglobin values and visual appearances of a range of blood conditions. A preferred blood gas control liquid has a density (at 20° C.) of about 1.08, facilitating its use in "open junction" types of blood gas analyzers where mixing of the blood gas control liquid and the potassium chloride electrolyte would interfere with and produce inaccurate measurement.

A preferred embodiment of the invention has the following formulation:

| Compound | Concentration |
|---|---|
| FC-77 | 10.95% (v/v) |
| FC-43 | 3.65% (v/v) |
| 200-1 | 19.8% (v/v) |
| Fluoroalkyl poly (ethyleneoxy) ethanol (Zonyl FSN) | 2.5% (v/v) |
| HEPES Buffer salts | 32.8 mM |
| NaOH | 30.50–35.23 mM |
| NaCl | 26.32–48.99 mM |
| Formaldehyde | 43.5 mM |

The first step in the preparation of this liquid was to prepare the antibacterial/surfactant/water solution by mixing together 1250 grams of 40% Zonyl FSN and 120 mL of formaldehyde and bringing the solution up to 16.0 liters with distilled water. The 200-1 silicone oil is then poured into the hopper of a Gaulin Homogenizer (Model 15M) and the aqueous phase is added at the rate of 725 mL/minute. The mixture is homogenized at a pressure of 2500 psig and repeatedly passed through an ice bath and recirculated to the hopper until all of the oil had been dripped into it. The pressure was then increased to 8000 psig and two discrete passes through the homogenizer are carried out to form a stable emulsion.

Next, an oil mixture was prepared by combining 2.20 L FC-77 with 0.73 L FC-43. The silicone emulsion was placed in the hopper of a Gaulin Homogenizer (Model 15M) and the fluorocarbon oil mixture was pumped into the hopper at the rate of 180 mL/min. while the liquid in the hopper was homogenized at a pressure of 2500 psig. The liquid was repeatedly passed through an ice bath and recirculated to the hopper until all of the oil had been dripped into it. At this point, the pressure was increased to 8000 psig and nine discrete passes through the homogenizer were carried out. A stable emulsion was formed by the ninth pass.

The emulsion was allowed to stand for 24 hours, and was then filtered through Whatman #3 filter paper using vacuum filtration with a Buchner funnel.

In a separate operation, buffers were prepared to be added to the emulsion. Three different buffers were made using HEPES, NaOH, and NaCl in different concentrations. After the buffers were added to the emulsions, each of the three emulsions was equilibrated with a different gas mixture, producing three different control liquids to be used under appropriate conditions. The three levels differed in pH, $pCO_2$, and $PO_2$, the levels having been chosen to reflect pH and gas partial pressure of the blood of normal patients, patients suffering from alkemia, and those suffering from acidemia. The three levels were:

| | Acidosis | Normal | Alkalosis |
|---|---|---|---|
| pH | 7.15–7.25 | 7.34–7.41 | 7.55–7.65 |
| $pCO_2$ | 65–75 mm Hg | 40–47 mm Hg | 18–24 mm Hg |
| $pO_2$ | 60–70 mm Hg | 95–110 mm Hg | 140–160 mm Hg |

The buffer formulations corresponding to the three levels were:

| | Acidosis | Normal | Alkalosis |
|---|---|---|---|
| NaOH | 30.50 mM/L emulsion | 33.91 mM/L | 35.23 mM/L |
| HEPES | 32.80 mM | 32.80 mM/L | 32.80 mM/L |
| NaCl | 26.32 mM | 48.99 mM/L | 48.94 mM/L |

The buffer formulations were added to the emulsion and each level was then given a distinctive color using the following dyes:

| Acidosis | Normal | Alkalosis |
|---|---|---|
| 1.667 g/L Red #33 | 1.25 g/L Red #33 | 0.781 g/L Red #33 |
| 3.333 g/L Yellow #5 | 1.25 g/L Yellow #5 | 1.406 g/L Yellow #5 |
| 0.01667 g/L Blue #1 | | |

The emulsions, containing dyes and dissolved buffer salts and having viscosities of about 8 centipoises (measured with a Brookfield Viscometer at 60 rpm-spindle #1), $O_2$ solubility coefficients of about 12.5, and densities of about 1.08 (at 20° C.), were then placed in a container which was thermally controlled to 25° C.±0.5° C. The appropriate equilibration gas mixture was then bubbled through each emulsion at the rate of 3 L/min. until the pH, $pO_2$, and $pCO_2$ reached equilibrium values, as determined by blood gas measuring equipment. The equilibration gas mixtures had the following compositions:

|  | Acidosis | Normal | Alkalosis |
|---|---|---|---|
| $CO_2$ | 6.7% | 4.15 | 2.0 |
| $O_2$ | 9.0% | 14.0 | 21.5 |
| $N_2$ | 84.3% | 81.85 | 76.5 |

After equilibration, glass ampuls which had been purged with the same gas equilibration mixture used for the emulsion were filled with 2 mL of the appropriate emulsion, up to below a hand-breakable line, and the ampuls heat-sealed.

The formulated control liquids, in their sealed ampuls, were used successfully to check the calibration of blood gas analyzers. An ampul containing the appropriate emulsion is opened and the control liquid is placed in the blood gas analyzer, which measures and registers the pH, $pCO_2$ and $pO_2$ of the emulsion. A reading outside of the pH and gas partial pressure ranges known to exist in the liquid indicates the need for re-calibration or repair of the analyzer.

The appearances and hemoglobin values of these formulated control liquids as set out in the following table:

|  | ABL 1 & 2 | IL 282 | Appearance |
|---|---|---|---|
| Acidosis | 17-22 g/dL | 11-14 g/dL | Normal venous blood |
| Normal | 14-18 | 8-12 | Normal arterial blood |
| Alkalosis | 8-12 | 6-9 | High $pO_2$, low hemoglobin blood |

Another embodiment of the invention has the following formulation:

| Compound | Concentration |
|---|---|
| FC-77 | 15% (v/v) |
| FC-43 | 5% (v/v) |
| Fluoroalkyl poly (ethyleneoxy) ethanol (Zonyl FSN) | 2% (v/v) |
| HEPES Buffer salts | 40 mM |
| NaOH | 38.7–42.57 mM |
| NaCl | 85.47–89.29 mM |
| Formaldehyde | 53 mM |

The first step in the preparation of this liquid was to prepare the antibacterial/surfactant/water solution by mixing together 500 grams of 40% Zonyl FSN and 60 mL of formaldehyde and bringing the solution up to 8.0 liters with distilled water. Next, an oil mixture was prepared by combining 1.5 L FC-77 with 0.5 L FC-43.

The aqueous solution was placed in the hopper of a Gaulin Homogenizer (Model 15M) and the oil mixture placed in a separatory funnel mounted above the hopper. Oil was dripped into the hopper at the rate of 100 mL/min. while the liquid in the hopper was homogenized at a pressure of 2500 psi. The liquid was repeatedly passed through an ice bath and recirculated to the hopper until all of the oil had been dripped into it. At this point, the pressure was increased to 8000 psi and nine discrete passes through the homogenizer were carried out. A stable emulsion was formed by the ninth pass.

The emulsion was allowed to stand for 24 hours, and was then filtered through Whatman #3 filter paper using vacuum filtration with a Buchner funnel.

In a separate operation, buffer solutions were prepared to be added to the emulsion. Three different buffer solutions were made using HEPES, NaOH, and NaCl in different concentrations. After the buffer solutions were added to the emulsions, each of the three emulsions was equilibrated with a different gas mixture, producing three different control liquids to be used under appropriate conditions. The three levels differed in pH, $pCO_2$, and $PO_2$, the levels having been chosen to reflect pH and gas partial pressure of the blood of normal patients, patients suffering from alkemia, and those suffering from acidemia. The three levels were:

|  | Acidosis | Normal | Alkalosis |
|---|---|---|---|
| pH | 7.15–7.25 | 7.34–7.41 | 7.55–7.65 |
| $pCO_2$ | 65–75 mm Hg | 40–47 mm Hg | 18–24 mm Hg |
| $pO_2$ | 60–70 mm Hg | 95–110 mm Hg | 140–160 mm Hg |

The buffer formulations corresponding to the three levels were:

|  | Acidosis | Normal | Alkalosis |
|---|---|---|---|
| NaOH | 38.7 mM/L emulsion | 40.62 mM/L | 42.57 mM/L |
| HEPES | 40.00 mM | 40.00 mM/L | 40.00 mM/L |
| NaCl | 89.29 mM | 87.38 mM/L | 85.43 mM/L |

The buffer formulations were added to the emulsion and each level was then given a distinctive color using the following dyes:

| Acidosis | Normal | Alkalosis |
|---|---|---|
| 100 mg/l Yellow #5 | 100 mg/l Amarath | 66.67 mg/l Amarath, 133.33 mg/l Yellow #5 |

The emulsions, containing dyes and dissolved buffer salts and having viscosities of about 4.5 centipoises, $O_2$ solubility coefficients of about 12.4, and a density of about 1.15 (at 20° C.), were then placed in a container which was thermally controlled to 25° C.±0.5° C. The appropriate equilibration gas mixture was then bubbled through each emulsion at the rate of 2 L/min. until the pH, $pO_2$, and $pCO_2$ reached equilibrium values, as determined by blood gas measuring equipment. The equilibration gas mixtures had the following compositions:

|  | Acidosis | Normal | Alkalosis |
|---|---|---|---|
| $CO_2$ | 7.0% | 4.17 | 1.98 |
| $O_2$ | 9.5% | 14.0 | 21.5 |
| $N_2$ | 83.5% | 81.83 | 76.52 |

After equilibration, glass ampuls which had been purged with the same gas equilibration mixture used for the emulsion were filled with 1 mL of the appropriate emulsion, up to below a hand-breakable line, and the ampuls heat-sealed.

Another embodiment of the invention employs a mixture of perfluoroalkanes and perfluorocyclic ethers (FC-77) and a polymer of about 20–25 units of polyethyleneoxide with between one and four tetrafluoroethylene groups at each end (Monflor 51). Two liters of FC-77 were emulsified, as described above for the FC-77/FC-43 emulsion, with an antibacterial surfactant/water solution consisting of 150 g Monflor 51 (about 1.5% by volume of emulsion) and 60 ml formaldehyde brought up to 8.00 liters with distilled water. After all the FC-77 had been added, the emulsion was subjected to seven discrete passes through the Gaulin Homogenizer.

Because Monflor 51 often contains HF as an impurity, the emulsions were neutralized with NaOH. After neutralization, buffers and dyes were added as described above for FC-77/FC-43, they were equilibrated with the appropriate gas mixtures, and the emulsions placed in ampuls. The liquids had viscosities of about 5 centipoises, $O_2$ solubility coefficients of about 13.5, and densities of about 1.15. In still another embodiment, liquids with stable emulsions of about 15% FC-77, 15% 200-1 silicone oil and Monflor 51 surfactant formulated and equilibrated as above described have densities of about 1.09, $O_2$ solubility coefficients of about 12.5, and viscosities of less than 10 centipoises.

The embodiments described above do not include added bicarbonate, but these emulsions nevertheless, owing to the gas equilibration step, effectively contain bicarbonate. Alternatively, it is of course possible to add bicarbonate, in appropriate amounts, along with HEPES.

The emulsions, in their sealed ampuls, were used successfully to check the calibration of blood gas analyzers. An ampul containing the appropriate emulsion is opened and the control liquid is placed in the blood gas analyzer, which measures and registers the pH, $pCO_2$ and $pO_2$ of the emulsion. A reading outside of the pH and gas partial pressure ranges known to exist in the liquid indicates the need for re-calibration or repair of the analyzer.

While particular embodiments of the invention have been described, various modifications will be apparent to those skilled in the art, and it is not intended that the invention be limited to the disclosed embodiments or to details thereof and departures may be made therefrom within the spirit and scope of the invention.

We claim:

1. A blood gas control product comprising a sealed container and a liquid composition of matter in said container, said composition of matter comprising
    a stable oil-in-water emulsion that includes water, a water insoluble non-protein organic compound material, and a non-ionic surfactant that is partially soluble in both said water and said compound material,
    a pH buffering agent, and
    a preservative present in a concentration sufficient to inhibit microbial growth in said blood gas control liquid without inpairing the quality control functions of said liquid, said preservative being substantially non-reactive with said buffering agent, said composition having a viscosity of less than ten centipoises and an oxygen solubility coefficient, at one atmosphere pressure and 25° C, of at least 10 ml $O_2$ per 100 ml liquid.

2. The product of claim 1 and further including a coloring agent to give said blood gas control liquid the appearance of normal arterial blood, said liquid having a partial pressure of oxygen of about 100 mm Hg, a partial pressure of carbon dioxide of about 45 mm Hg, and a pH of about 7.4.

3. The product of claim 1 and further including a coloring agent to give said blood gas control liquid the appearance of normal venous blood, said liquid having a partial pressure of oxygen of about 65 mm Hg, a partial pressure of carbon dioxide of about 70 mm Hg, and a pH of about 7.2.

4. The product of claim 1 and further including a coloring agent to give said blood gas control liquid the appearance of low hemoglobin, high $pO_2$ blood, said liquid having a partial pressure of oxygen of about 150 mm Hg, a partial pressure of carbon dioxide of about 21 mm Hg, and a pH of about 7.6.

5. The product of claim 1 wherein said preservative is an aldehyde, and said buffering agent includes a tertiary amine.

6. The product of claim 5 wherein said aldehyde is formaldehyde, and said tertiary amine is HEPES.

7. The product of any one of claims 2, 3 or 4 wherein said coloring agent is selected from the class consisting of Red #33, Yellow #5, Blue #1 and Amarath, and mixtures thereof.

8. The product of any one of claims 2, 3 or 4 wherein the density of said composition is about 1.08.

9. The product of claim 1 wherein said compound material includes a perfluorinated compound material that has an oxygen solubility coefficient, at one atmosphere pressure, 25° C., and a volumetric proportion of 15%, of at least 10 ml $O_2$ per 100 ml liquid.

10. The product of any one of claims 1, 2, 3 or 4 wherein the density of said composition is less than 1.12.

11. A blood gas control product comprising a sealed container and a liquid composition of matter in said container, said composition of matter comprising
    a stable oil-in-water emulsion that comprises water, 5-40% by volume of a water-insoluble perfluorinated compound material, said emulsion having an oxygen solubility coefficient, at one atmosphere pressure and 25° C., of at least 10 ml $O_2$ per 100 ml liquid, and
    0.25-10% by volume of a non-ionic fluorocarbon-based surfactant capable of emulsifying said perfluorinated compound material,
    a pH buffering agent, and
    a preservative present in a concentration sufficient to inhibit microbial growth in said blood gas control liquid without impairing the quality control functions of said liquid, said preservative being substantially non-reactive with said buffering agent,
    said blood gas control liquid having a viscosity of less than ten centipoises, a pH in the range of 7.0 to 8.0, a partial pressure of $CO_2$ in the range of 15-80 mm Hg, and a partial pressure of $O_2$ in the range of 20-600 mm Hg.

12. The product of claim 11 wherein the density of said composition is about 1.08.

13. The product of any one of claims 12, 9 or 11 wherein said composition contains less than 25% by volume of said perfluorinated compound material, less than 5% by volume of said surfactant, said preservative includes and aldehyde, said buffering agent includes a tertiary amine, a partial pressure of oxygen in the range of 50-80 mm Hg, and said composition further includes a coloring agent selected from the class consisting of Red #33, Yellow #5, Blue #1 and Amarath, and mixtures thereof.

14. The product of either claim 6 or 9 wherein said compound material comprises a mixtures of perfluoroalkanes, perfluorocyclic ethers, and perfluorotributylamine, and said non-ionic surfactant comprises fluoroalkylpoly(ethyleneoxy) ethanol.

15. The product of either claim 6 or 9 wherein said compound material comprises a mixture of perfluoroalkanes and perfluorocyclic eithers, and said non-ionic surfactant comprises a fluorocarbon-based polymer of about 20–25 units of polyethylene oxide with between one and four tetrafluoroethylene groups at each end.

16. The blood gas control product of claim 14 wherein said perfluoroalkanes and perfluorocyclic ethers together comprise about 15% by volume of said liquid, said perfluorotributyl amine comprises about 5% by volume of said liquid, said fluoroalkylpoly(etheleneoxy) ethanol comprises about 2% by volume of said liquid, said preservative is formaldehyde present in a concentration of about 53 mM, and said product further comprises at least one dye.

17. The blood gas control product of claim 14 wherein said perfluoroalkanes and perfluorocyclic ethers together comprise about 11% by volume of said liquid, said perfluorotributyl amine comprises about 3.6% by volume of said liquid, said fluoroalkylpoly(etheleneoxy)ethanol comprises about 2.5% by volume of said liquid, said preservative is formaldehyde present in a concentration of about 43 mM, and said product further comprises about 20% by volume of a silicone oil and at least one dye.

18. The blood gas control product of claim 15 wherein said perfluoroalkanes and perfluorocyclic ethers together comprise about 20% of said liquid, said non-ionic polymeric, fluorocarbon-based surfactant comprises about 2% of said liquid by volume, and said preservative is formaldehyde present in a concentration of about 53 mM, and said product further comprises at least one dye.

19. The product of either claim 1 or 11 wherein the density of said composition is less than 1.12 and said emulsion further includes 15–25% by volume of a silicone oil.

20. The product of any one of claims 12, 9 or 11 wherein said composition contains less than 25% by volume of said perfluorinated compound material, less than 5% by volume of said surfactant, said preservative includes an aldehyde, said buffering agent includes a tertiary amine, a partial pressure of oxygen in the range of 90–115 mm Hg, and said composition further includes a coloring agent selected from the class consisting of Red #33, Yellow #5, Blue #1 and Amarath, and mixtures thereof.

21. The product of any one of claims 12, 9 or 11 wherein said composition contains less than 25% by volume of said perfluorinated compound material, less than 5% by volume of said surfactant, said preservative includes an aldehyde, said buffering agent includes a tertiary amine, a partial pressure of oxygen in the range of 130–170 mm Hg, and said composition further includes a coloring agent selected from the class consisting of Red #33, Yellow #5, Blue #1 and Amarath, and mixtures thereof.

* * * * *